United States Patent
Caramella et al.

(10) Patent No.: US 6,355,272 B1
(45) Date of Patent: Mar. 12, 2002

(54) COMPLEX BETWEEN CARRAGEENAN AND A WATER SOLUBLE DRUG HAVING A SPECIFIC GRANULOMETRY AND RELATIVE CONTROLLED RELEASE PHARAMACEUTICAL COMPOSITIONS

(75) Inventors: Carla Marcella Caramella; Maria Cristina Bonferoni, both of Pavia (IT)

(73) Assignee: Eurand International S.p.A. (IT)

(*) Notice: Subject to any disclaimer, the term of this patent is extended or adjusted under 35 U.S.C. 154(b) by 0 days.

(21) Appl. No.: 09/530,245

(22) PCT Filed: Oct. 29, 1998

(86) PCT No.: PCT/EP98/06864

§ 371 Date: Apr. 26, 2000

§ 102(e) Date: Apr. 26, 2000

(87) PCT Pub. No.: WO99/21586

PCT Pub. Date: May 6, 1999

(30) Foreign Application Priority Data

Oct. 29, 1997 (IT) ......... PV97A0009

(51) Int. Cl.$^7$ ............ A16K 9/14; A16K 9/20; A16K 9/22; A16K 9/24

(52) U.S. Cl. ......... 424/489; 424/464; 424/468; 424/472

(58) Field of Search ............ 424/464, 468, 424/489, 472

(56) References Cited

U.S. PATENT DOCUMENTS

| | | | | |
|---|---|---|---|---|
| 3,558,768 A | * | 1/1971 | Klippel | 424/21 |
| 5,132,116 A | * | 7/1992 | Sournac | 424/469 |

FOREIGN PATENT DOCUMENTS

| | | |
|---|---|---|
| EP | 0091409 | 10/1983 |
| EP | 0091409 A | * 10/1983 |
| EP | 0153836 | 9/1985 |
| GB | 1183403 | 3/1970 |
| JP | 60174729 | 9/1985 |
| JP | 61130239 | 6/1986 |
| WO | 8400294 | 2/1984 |
| WO | 9307860 | 4/1993 |

OTHER PUBLICATIONS

Journal of Controlled Release, vol. 26, No. 2, Aug. 1, 1993, pp. 119–127, Bonferoni M C et al., "On The Employment OJF—Carregeenan in a Matrix System. I Sensitivity to Dissolution Medium and Comparison with NA Carboxymethycellulose and Xanthan Gum".*

Journal of Controlled Release, vol. 26, No. 2, Aug. 1, 1993, pp. 119–127, Bonferoni M C et al., "On the Employment of —Carrageenan in a Matrix System. I Sentsitivity to Dissolution Medium and Comparsion with NA Carboxymethycellulose and Xanthan Gum".

Journal of Controlled Release, vol. 30, No. 2, May 1, 1994, pp. 175–182, Bonferoni M C et al., "On the Employment of Lambda–Carrageenan in a Matrix System II. Lamboa–Carrageena and Hydroxyprolymethycellulose Mixtures".

Horace D. Graham, et al., "Complex Formation Between Hydrocolloids and Tranquilizers and Hypotensive Agents", Journal of Pharmaceutical Sciences, vol. 52, No. 2, Feb. 1963, p. 192–198.

* cited by examiner

Primary Examiner—Thurman K. Page
Assistant Examiner—Rachel M. Bennett
(74) Attorney, Agent, or Firm—Thompson Hine LLP

(57) ABSTRACT

A complex between carrageenan and a water soluble drug characterized in powder form having an average particle size comprised between 10 and 100 μm, and the basic water drug is contained in the complex in amounts ranging from 1.5 and 5 mmol/g carrageenan, a process for preparing this complex and relative controlled release pharmaceutical compositions containing it.

28 Claims, 5 Drawing Sheets

COMPLEX BETWEEN CARRAGEENAN AND A WATER SOLUBLE DRUG HAVING A SPECIFIC GRANULOMETRY AND RELATIVE CONTROLLED RELEASE PHARAMACEUTICAL COMPOSITIONS

This application is a 371 of PCT/EP98/06864 filed Oct. 29, 1998.

FIELD OF THE INVENTION

The present invention relates to a complex between a water soluble drug and carrageenan in powder form characterised in that this powder has a specific granulometry, a process for preparing this complex and controlled release pharmaceutical composition containing said complex.

PRIOR ART DISCLOSURE

One of the simplest and cheapest methods to obtain the prolonged release of drugs is the use of tablets containing the drug and one or more polymers quite often able to gelify. Especially in the case of very soluble drugs, however, the release rate is higher at the beginning of the dissolution and decreases with the increase in diffusional pathway. This can result in strong variations of plasma levels especially in the case of drugs administered at high dosages.

Solid oral dosage forms based on ion exchangers are described in the literature. Ionic exchange resins and hydrophilic polymers with ionisable groups have been used. Most of the commonly used drugs, being basic in nature, can interact with polymer acidic groups (carboxylic or sulfonic groups). The sulfonic polymers, being stronger acids, are likely to interact with the drug independently of the pH of the medium. In any case, the ionic interaction between the drug and the polymer gives as a result a change of the release profiles of the drug. In particular, with some drugs a precipitation of the complex may occur.

Drug-carrageenan complexes have been proposed for the sustained release in parenteral administration (intramuscular) (H. D. Graham et al, J. Pharm. Sci, 52,1963, 193–198).

Moreover, complexes of carrageenan with some drugs (emepronium, doxicicline and propranolol) and with antidepressant drugs have been proposed to reduce the risks of overdosing the drug (WO 93/07860, 1993).

An ofloxacin-carrageenan complex has also been proposed to prepare sustained release tablets, whose release was completed in 2–3 hours (JP 61 130239, 1986). In the methods of complex preparation described in the literature at least one of the interacting species is present in solution; in some cases polymer solutions concentrated at 5% w/v are used (JP 60 174729).

However, in the preparation of solid oral dosage forms (tablets, pills, capsules, granulates), no particular attention has been given, until now, to the particle size of the complex, and quite often high amounts of other excipients have been used to obtain coherent tablets or to slow down the release rate.

Controlled release tablets have many advantages from the technological point of view and for the patient compliance. A thorough formulation study is however necessary to obtain the desired release rate and profile also taking into account the characteristics, for example the pH, of the dissolution medium. When high dosages of a freely soluble drug are needed, this task is rendered more difficult since the quantity of polymers and other excipients to be added to modulate the release must be limited, in order to avoid the preparation of tablets of big dimensions.

TECHNICAL PROBLEM

The need was felt to have controlled release therapeutical compositions not containing high amounts of polymers and excipients and therefore being of acceptable dimensions for the oral administration.

SUMMARY OF THE INVENTION

The present invention relates to a complex of carrageenan with a water soluble drug in powder form with an average particle size ranging from 10 to 100$\mu$ and the basic water soluble drug is contained in the complex in amounts ranging from 1.5 and 5 mmol/g carrageenan.

The Applicant has in fact surprisingly found that by using the carrageenan complex with the average particle size in the above mentioned range it is possible to prepare controlled release pharmaceutical compositions not suffering from the drawbacks of the above mentioned known controlled release pharmaceutical compositions containing the carrageenan complex.

In fact by using the carrageenan complex according to the present invention it is possible to prepare controlled release pharmaceutical compositions without the need to add high quantities of further excipients or polymers able to further slow down the drug release.

The present invention therefore further relates to controlled release pharmaceutical compositions containing the complex according to the present invention.

The invention also concerns a process for preparing the complex, based on the interaction between polymer and drug when a minimum amount of water is added, therefore unlikely the known processes above reported, it does not require a previous dissolution of the carrageenan and/or the drug in water.

In particular this process according to the present invention comprises the following steps:

a) preparing a homogeneous mixture of drug and carrageenan in suitable quantities in order to obtain a final carrageenan complex wherein the drug is contained amounts comprised between 1.5 and 5 mmol/g carrageenan b) kneading the mixture in a suitable apparatus by adding a water content expressed as weight ratio water/polymer+water soluble basic substance comprised between 1:3 and 3:1 c) optionally washing the product coming from step (b);

d) drying the mixture.

e) milling the dried product until reaching the desired particle size.

The advantages of the process according to the present invention which does not require a previous solubilization step can be summarised as follows:

the recovery of the complex is much easier than in the prior art processes using high volumes of solvent;

process times are decidedly shorter;

the centrifugation or filtration step of highly viscous carrageenan solution to recover the desired complex is no longer strictly necessary.

DESCRIPTION OF THE FIGURES

FIG. 2-B reports the release profiles at pH 6.8 of the tablet prepared as described in Example 3 and the tablet prepared as described in Example 2 (209), having a sieve fraction <45 µm, wherein the percentage of drug release is reported in ordinates and the time in hour is reported in abscissae.

FIG. 3-B reports the release profile at pH 1.2 and 6.8 of the tablet prepared as described in Example 2 prepared with the complex of carrageenan with diltiazem, having a particle size 45–75 µm, wherein the percentage of drug release is reported in ordinates and the time in hour is reported in abscissae.

FIG. 4-B reports the release profile at pH 7.5 of the tablet prepared as disclosed in Example 6 with the complex of carrageenan with propranolol having either a particle size 45–75 µm or <45 µm, wherein the percentage of drug release is reported in ordinates and the time in hour is reported in abscissae.

DETAILED DESCRIPTION OF THE INVENTION

Figure 1:
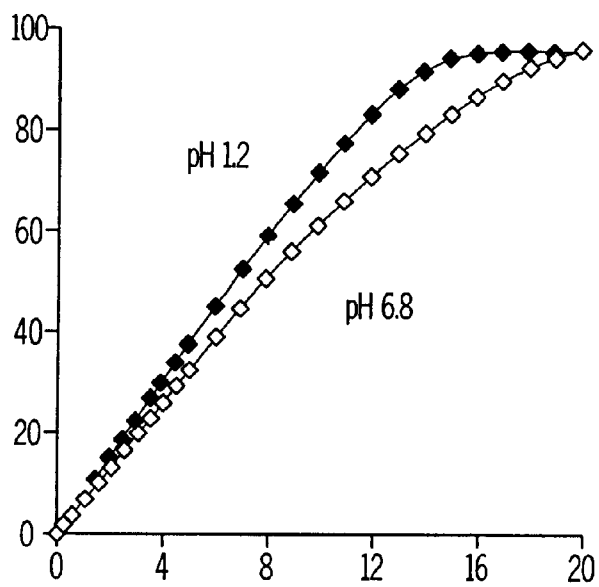
FIG. 1 reports the release profiles at pH 1.2 and pH 6.8 of the tablet prepared as described in Example 7 with the complex of carrageenan with diltiazem·HCl, wherein the percentage of drug release is reported in ordinates and the time in hour is reported in abscissae.

As previously pointed out the Applicant has found that the granulometric range of the complex according to the present invention is critical in order to obtain a controlled drug release. In fact with pharmaceutical composition essentially based on the carrageenan complex with a particle size higher than 100 µm it is not possible to modulate the drug release, since the drug is very quickly released, by contrast using a pharmaceutical composition containing as the essential component a complex having an average granulometry below 10 µm, the drug release is very slow and moreover the milling, to obtain this very fine granulometry, is tedious and rather expensive.

The Applicant has in any case found that better results can be achieved by using carrageenan complexes having a particle size comprised between 45 and 75 µm and <45 µm.

The content of the basic water soluble drug is preferably contained in amounts in the complex ranging from 3.0 to 4.0 mmol/g.

The basic water soluble drug is preferably selected from the group consisting of analgesics, antiparkinsonians, antiinflammatory agents, anaesthetics, antimicrobials, antimalarics, antiparasitics, anticonvulsivants, CNS drugs, diuretics, hypnotics, tranquillisers, sedatives, muscle relaxants, hormones, contraceptives, sympathomimetics, hypoglicemic agents, ophtalmics, cardiovasculars.

According to a preferred embodiment in the complex according the present invention the basic drug is selected from the group consisting of: diltiazem promethazine, salbutamol, chlorpheniramine propranolol and/or pharmaceutically acceptable salts thereof.

According to a particularly preferred embodiment the basic drug is selected from the group consisting of: diltiazem HCl, promethazine HCl, salbutamol sulphate, chlorpheniramine maleate.

The carrageenan to be used may be indifferently the iota kappa or lambda type, although better results are obtained by using lambda carrageenan.

The carrageenan in the complex according to the present invention has preferably a viscosity comprised between 500 and 2000 cPs, more preferably has a viscosity ranging from 700 to 1600 cPs measured at 37° C. with a shear rate of 20 s exp(−1). According to a particularly preferred embodiment carrageenan is used available in the market with the trademark Viscarin® GP 209 having a viscosity of 1598 cPs. measured at 37° C. with a shear rate of 20 s exp(−1).

The controlled release pharmaceutical compositions according to the present invention contain the complex according to the present invention in amounts ranging from 60 to 100%, more preferably in amounts ranging from 80 to 100% by weight based on the total composition weight.

The controlled release pharmaceutical compositions according to the present invention show a further advantage since their drug release is independent from the pH of the medium.

The employment of the complex at a well defined particle size (under 100 µm) allows to prepare controlled release tablets containing up to 90–100% complex, and therefore 60–80% of drug (depending on the maximum binding capacity of the polymer and on the molecular weight of the drug). These tablets can therefore be exploited also in case of high drug dosages, such as those necessary for once-a-day administration.

The controlled release may optionally contain up to 5%, preferably between 1 and 4% by weight based on the total composition weight of a gellable polymer selected from the group consisting of hydroxypropylmethylcellulose hydroxypropylcellulose having a viscosity comprised between 4000 and 100,000 cPs, in order to further modulate the drug release.

The controlled release pharmaceutical composition according to the present invention may be in the form of tablets, pellets and granules. The pellets or granules can be used for the preparation of extemporaneous aqueous suspension, or may be contained in hard or soft capsules.

According to a preferred embodiment the controlled release pharmaceutical compositions are preferably in the form of tablets. The employment of small particle size fractions (45–75 µm or <45 µm) reduces the release rate, also from tablets made with the complex alone, to values that are suitable for once a day administration, meaning a release completed within 20–24 h. Moreover, it has been shown that almost linear release profiles and at any rate a marked reduction in burst effect, quite independently of medium pH, can be achieved.

These tablets may be prepared by direct compression of the complex powder or by compression of granules obtained by wet granulation with the process disclosed later on for the preparation of granules. The flow properties of fine fractions may render the granulation step and the addition of glidants (such as talc) to the granulate necessary; a composition useful for this kind of procedure is described in Example 7: hydroxypropylmethylcellulose (5% Methocel K4M mixed to the complex and 2–3% Methocel E15 dissolved in the binding solution) has been used. The release profiles obtained with this formulation are given in FIG. 1. The release occurs at approximately constant rate during about 20 h both in pH 1.2 (gastric) and in pH 6.8 (intestinal) buffers.

The Applicant has also surprisingly found that the tablets having the ratio surface/volume R comprised between 0.7 and 0.9 are preferred as concerns the controlled release profiles.

The pellets have preferably an average particle size ranging from 1 to 3 mm and the granules have an average particle size ranging from 0.2 to 1 mm. Both granules and pellets are prepared by using conventional techniques encompassing the following steps:

(i) kneading the carrageenan complex powder according to the present invention with an alcoholic solvent in the presence of a binder such as ethyl or methylcellulose having a viscosity ranging from 10 to 100 cPs, (ii) granulating the kneaded mixture in a suitable granulator such as a rotogranulator, (iii) drying the wet granules or pellets, (iv) classification of the granules to separate the granules or pellets having the desired average particle size.

The present invention further relates to controlled release pharmaceutical composition in the form of a tablet containing a:

A) a core

B) an external layer completely or partially covering the core tablet containing the carrageenan complex with the basic water soluble drug according to the present invention, said external layer being applied by compression.

Preferably this external layer contains the complex according to the present invention in amounts ranging from 60 to 100%, preferably in amounts ranging from 80 to 100%.

It may optionally contain up to 5%, preferably between 1 and 4% by weight based on the total composition weight of a gellable polymer selected from the group consisting of hydroxypropylmethylcellulose having a viscosity comprised between 4000 and 100,000 cPs., in order to further modulate the drug release.

In step (b) of the process according the present invention the water to be added expressed as weight ratio water/polymer+water soluble basic substance is preferably comprised between 1:2 and 2:1.

The following examples of preparation of the complex according to the present invention are reported for illustrative, but not limitative purposes.

EXAMPLE 1

100 g of carrageenan (Viscarin GP 209, FMC) and 128 g of promethazine.HCl are mixed in a turbula mixer. The minimum amount of water necessary to knead the mixture is added (about 100 ml). The complex is separated by centrifugation at 2000 rpm for 10 minutes, and washed with distilled water. The solid product is lined in trays, dried in oven at 40–50° C. overnight and milled.

EXAMPLE 2

1000 g of carrageenan (Viscarin GP 209, FMC) and 1000 g of diltiazem·HCl are mixed in a turbula mixer. The minimum amount of water necessary to knead the mixture is added (about 1000 ml). The complex is separated by centrifugation, and washed with distilled water. The solid product is lined in trays, dried in oven at 40–50° C. overnight and milled. The sieve fractions 45–75 $\mu$m and 75–105 $\mu$m and <45 $\mu$m are obtained. 300 mg weight tablets, each containing about 180 mg of diltiazem·HCl, are prepared by means of an hydraulic press Perkin Elmer, at 3 tons (1 minute) with 10 mm diameter flat punches.

EXAMPLE 3

1000 g of low viscosity carrageenan (Viscarin GP 109, FMC) and 1600 g of diltiazem·HCl are mixed in turbula mixer. The minimum amount of water necessary to knead the mixture is added (about 1000 ml). The complex is separated by centrifugation, and washed with distilled water. The solid product is lined in trays, dried in oven at 40–50° C. overnight and milled and sieved in order to recover the fraction having particle size <45 microns. 300 mg weight tablets are prepared, each containing about 180 mg of diltiazem·HCl, by means of an hydraulic press Perkin Elmer, at 3 tons (1 minute) with 10 mm diameter flat punches.

EXAMPLE 4

100 g of carrageenan (Viscarin GP 209, FMC) and 45 g of salbutamol sulphate are mixed in a turbula mixer. About 200 ml of water are added to the mixture, that is kneaded until achieving a homogeneous mixture. The complex is lined in trays, dried in oven at 40–50° C. overnight and milled up to the desired granulometry.

EXAMPLE 5

100 g of carrageenan (Viscarin GP 209, FMC) and 75 g of chlorpheniramine maleate are mixed in turbula mixer. About 150 ml of water are added to the mixture, that is kneaded until achieving a homogeneous mixture. The complex is lined in trays, dried in oven at 40–50° C. overnight and milled up to the desired granulometry.

EXAMPLE 6

1000 g of carrageenan (Viscarin GP 209, FMC) and 1600 g of propranolol are mixed in a turbula mixer. The minimum amount of water necessary to knead the mixture is added (about 1000 ml). The complex is separated by centrifugation, and washed with distilled water. The solid product is lined in trays, dried in oven at 40–50° C. overnight and milled. The sieve fractions 45–75 $\mu$m and 75–105 $\mu$m are obtained. 300 mg weight tablets, containing about 150 mg propranol, are obtained by means of an hydraulic press Perkin Elmer, at 3 tons (1 minute) with 10 mm diameter flat punches.

EXAMPLE 7

From the complex obtained as described in the example 2, the <45 $\mu$m sieve fraction is obtained. A mixture containing 95% of this fraction and 5% of HPMC Methocel K4M is granulated by wetting with a solution of HPMC Methocel E15 and extrusion through 700 μm sieve, and is dried in oven. The granulate is forced through a 700 μm sieve again and 2% talc is added. Respectively 300 mg tablets, containing about 180 mg of diltiazem·HCl, are obtained by means of an alternative Kilian KIS tabletting machine, with convex 11 mm punches.

EXAMPLE 8

From the granulate prepared as described in Example 7, 570 mg tablets containing 300 mg diltiazem·HCl were obtained with a Kilian KIS tabletting reciprocating machine equipped with either 11 mm convex punches with surface/volume ratio R=0.7 or 13 mm flat punches (surface/volume ratio R=0.9).

Methods for Carrying Out the Tests of Drug Release in vitro

The release test of some of the tablets prepared according to the above reported examples was performed in a 1 basket USP XXIII apparatus at 100 rpm 37° C. using either a 500 or 1000 ml fluid. The following tests had been conducted A) The test at pH 1.2 simulating the gastric fluid(USPXIII without enzymes).

B) The test carried out at pH 6.8 and 7.5 simulating the intestinal fluid.

C) The test carried out changing the pH from 1.0 to 6.8 (0.1 M HCl to 6.8 by adding $Na_3PO_4$ 0.2M) after 3 hours from dissolution.

Results

Figure 2A:
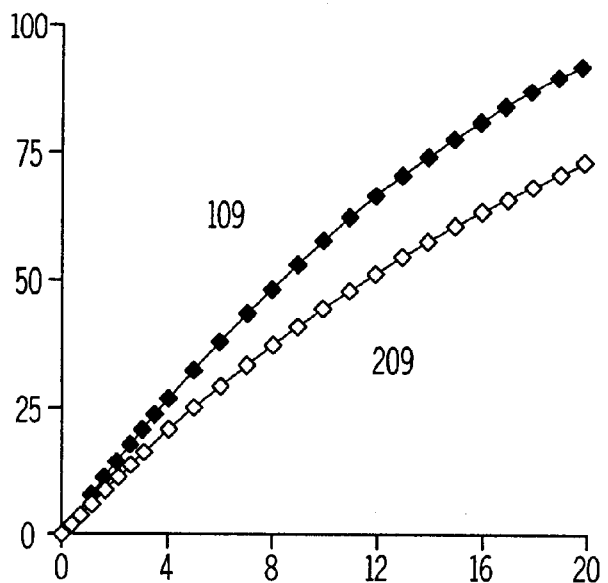
FIG. 2-A reports the release profiles at pH 1.2 of the tablet prepared as described in Example 3 (109) and the tablet prepared as described in Example 2 (209) having a sieve fraction <45 µm, wherein the percentage of drug release is reported in ordinates and the time in hour is reported in abscissae.
Figure 2B:
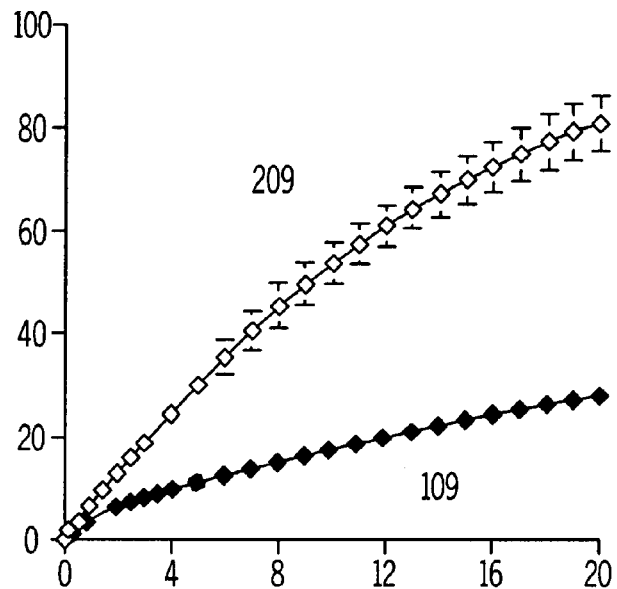
Figure 3A:
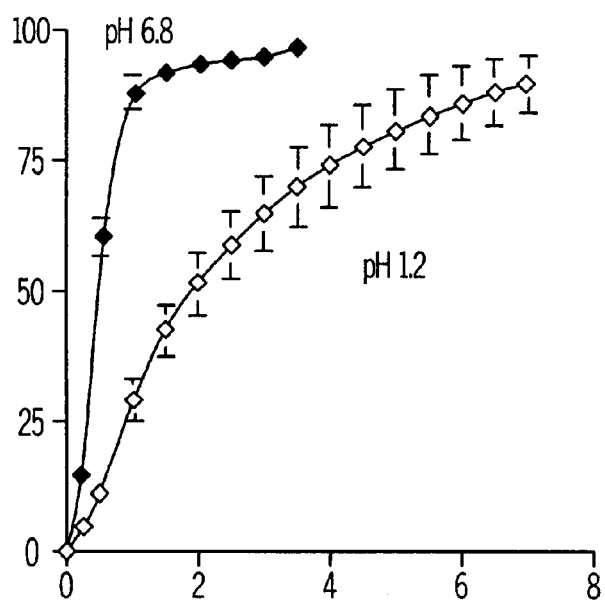
FIG. 3-A reports the release profile at pH 1.2 and 6.8 of the tablet prepared as described in Example 2 prepared with the complex of carrageenan with diltiazem·HCl, having a particle size 75–105 µm, wherein the percentage of drug release is reported in ordinates and the time in hour is reported in abscissae.
FIG. 3C reports the release profile at pH 1.2 and 6.8 of the tablet prepared as described in Example 2 with the complex of carrageenan with diltiazem having a particle size <45 µm, wherein the percentage of drug release is reported in ordinates and the time in hour is reported in abscissae.
Figure 3B:
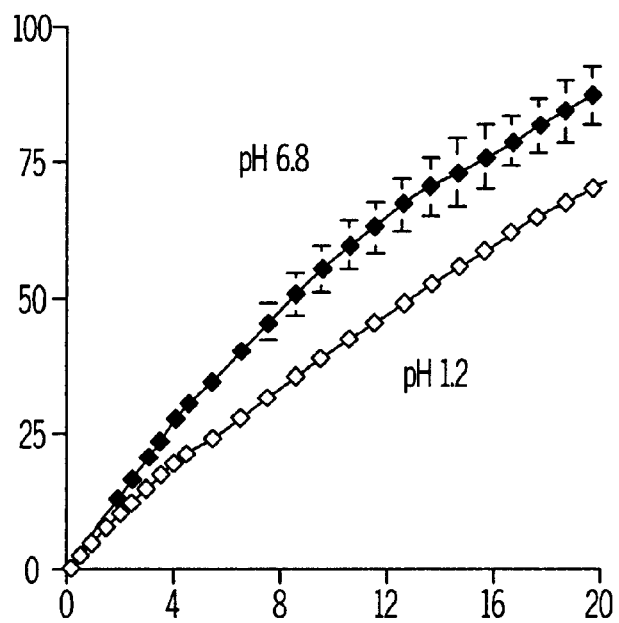
Figure 3C:
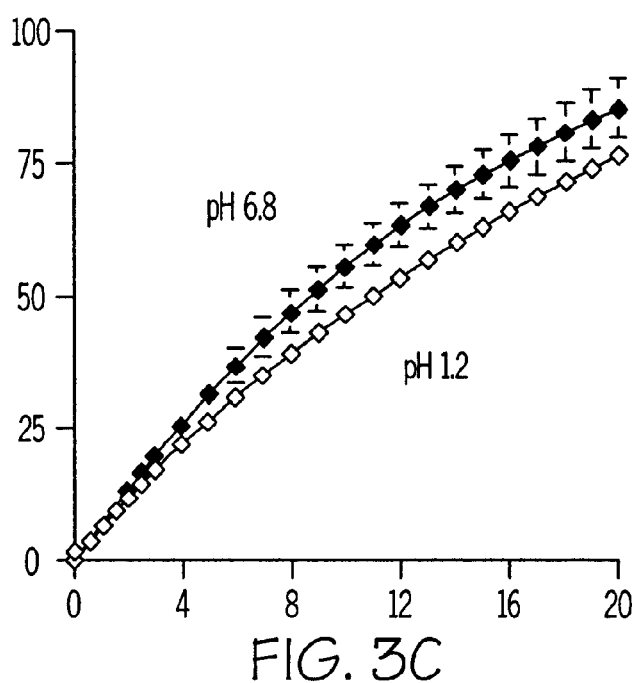
Figure 4A:
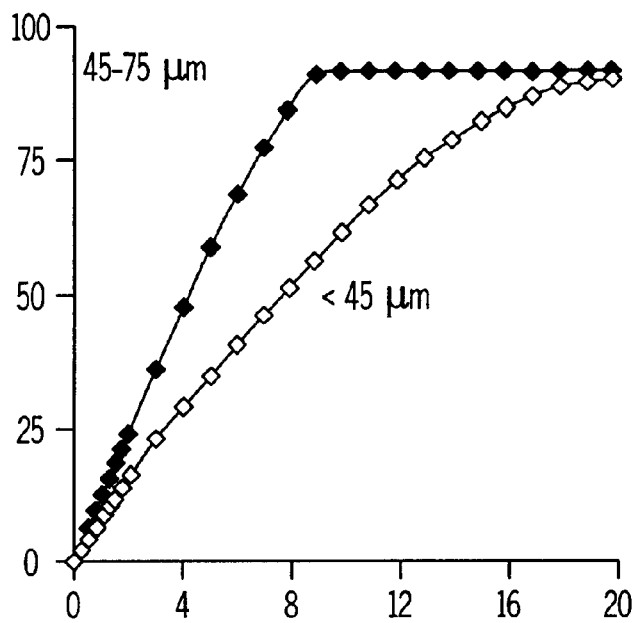
FIG. 4-A reports the release profile at pH 1.2 of the tablet prepared as disclosed in Example 6 with the complex of carrageenan with propranolol having a particle size either 45–75 µm or <45 µm, wherein the percentage of drug release is reported in ordinates and the time in hour is reported in abscissae.
Figure 4B:
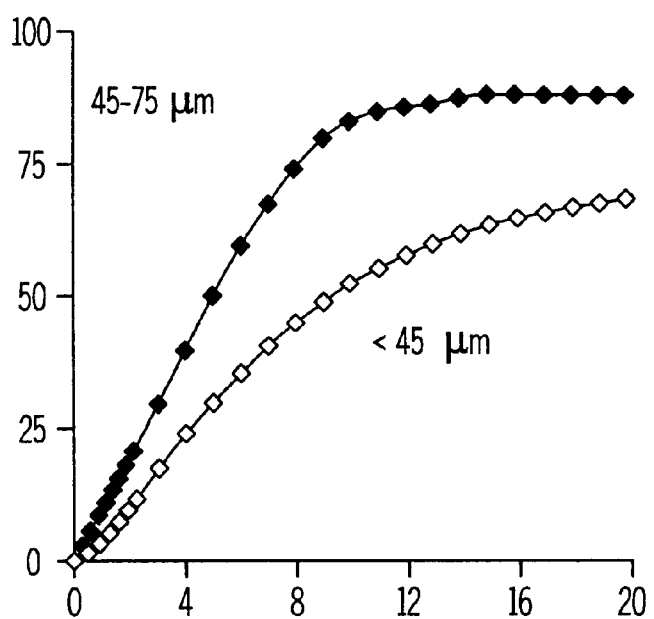
Figure 5:
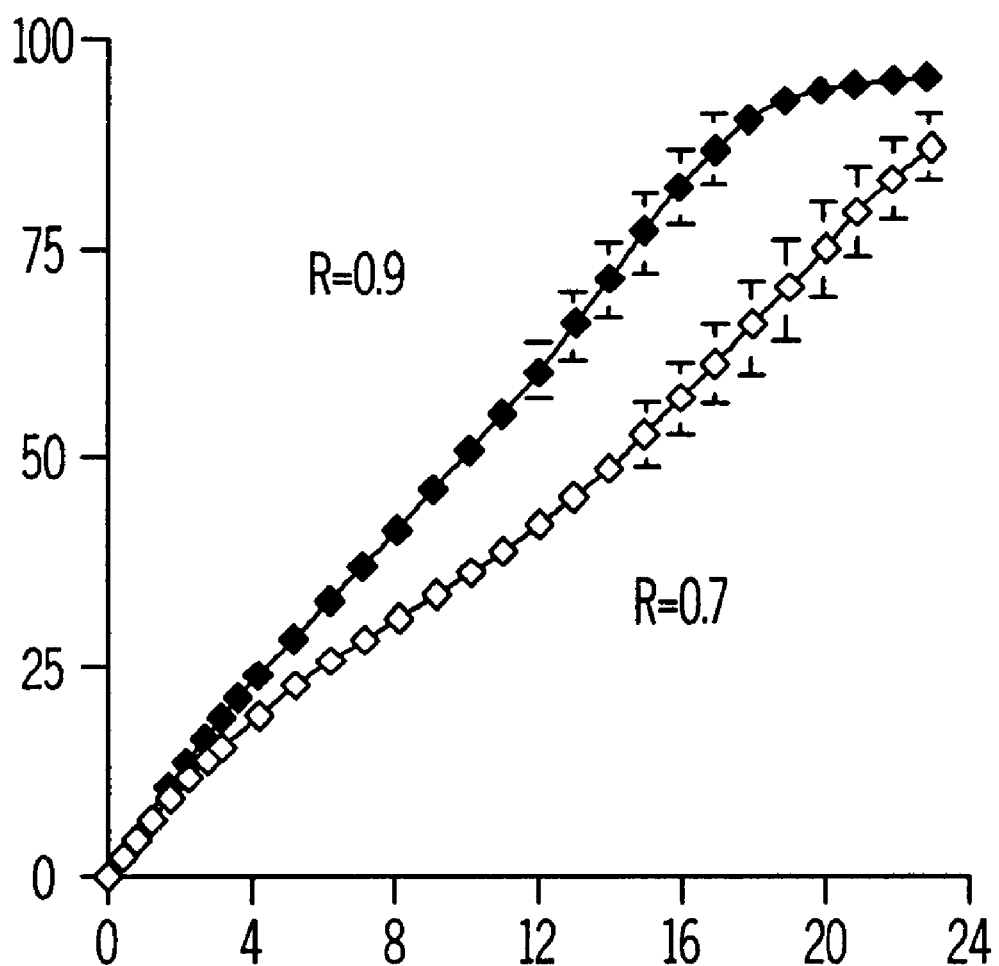
FIG. 5 reports the release profile carried out in the dissolution test conducted with a pH change after 3 hours from dissolution of tablets whose preparation is disclosed in Example 8 having surface/volume ratio R of 0.7 and 0.9.

The results of the above tests are reported in FIG. 1, FIGS. 2A, 2B, FIGS. 3A–3B, 3-C, FIGS. 4A–4B, FIG. 5.

In particular FIG. 1 reports the results of test A and B carried out on tablets whose preparation is disclosed in Example 7 containing therefore besides the carrageenan complex with diltiazem·HCl having a particle size lower than 45 μm also small amounts of talc and hydroxypropylmethylcellulose. As one can observe from this figure there is no substantial variation between the release at pH 1.2 and pH 6.8. This means that the tablets prepared according to example 7 are insensible to the pH medium and the release of the drug is complete at both the above mentioned pH after 20 hours from dissolution.

FIG. 2A reports the drug release profile at pH 1.2 of tablets obtained according to Example 3 consisting of a complex between Diltiazem·HCl and carrageenan VISCARIN® GP 109 having a viscosity of 761 cPs measured at 37° C. with a shear rate of 20 s exp(−1) and compared with tablets prepared as described in Example 2 with the complex between Diltiazem·HCl having a particle size <45 μm and carrageenan (VISCARIN® GP 209) having a viscosity of 1598 cPs, wherein it results that at low pH the Diltiazem·HCl complex with carrageenan with higher viscosity have a similar release profile if compared with the corresponding one with lower viscosity, although a little better results are obtained with the complex whose carrageenan has a low viscosity.

FIG. 2B reports the drug release profile at pH 6.8 of tablets obtained according to Example 3 obtained by a complex between Diltiazem·HCl and carrageenan VISCARIN® GP 109 having a viscosity of 761 cPs calculated at 37° C. with a shear rate of 20 s exp(−1) and compared with tablets prepared as described in Example 2 with the complex between Diltiazem·HCl having a particle size <45 μm and carrageenan (VISCARIN®209) having a viscosity of 1598 cPs, wherein it results that at pH 6.8 the complex with carrageenan having higher viscosity gives good results, by contrast in the complex prepared with carrageenan having lower viscosity the release is very slow and after 20 hours only 20% of the drug is released.

FIGS. 3A–3C reports the drug release profile at pH 1.2 and 6.8 as a function of granulometry wherein it results that for the carrageenan complex with diltiazem·HCl having a granulometry comprised between 75 and 105 μm only at pH 1.2 it is possible to control in some way the release of the drug. In fact the drug is completely released after 8 hours. By contrast at pH 6.8 the same complex completely releases the drug in about 90 minutes. With complexes having granulometry comprised between 45 and 75 μm but also <45 μm both at pH 1.2 and at pH 6.8 it is possible to slow down the diltiazem release up to 20 hours from dissolution.

Comparable results may be achieved with complexes between propranol and carrageenan reported in FIGS. 4A and 4(B), although better results can be achieved with the complex fraction whose granulomtery is <45 μm at both pH.

FIG. 5 demonstrates that good results are obtained with tablets having the ratio surface/volume R comprised between 0.7 and 0.9 although better results are obtained with the tablets having this ratio R=0.7, since the release is completed in 24 hours.

What is claimed is:

1. A complex of carrageenan having a viscosity comprised between 500 and 2000 cPs. measured at 37° C. with a shear rate of 20 s exp(−1); with a water soluble drug in powder form with an average particle size ranging from 10 to 100μ and the basic water soluble drug is contained in the complex in amounts ranging from 1.5 and 5 mmol/g carrageenan.

2. The carrageenan complex according to claim 1 having an average particle size <45 μm.

3. The carrageenan complex according to claim 1 having a particle size comprised between 45 and 75 μm.

4. The complex according to claim 1 wherein the basic water soluble drug is preferably contained in amounts ranging from 3.0 to 4.0 mmol/g.

5. The complex according to claim 1 wherein the basic water soluble drug is preferably selected from the group consisting of analgesics, antiparkinsonians, anti-inflammatory agents, anesthetics, antimicrobials, antimalarics, antiparasitics, antioconvulsivants, CNA drugs, diuretics, hypnotics, tranquillisers, sedatives, muscle relaxants, hormones, contraceptives, sympathomimetics, hypoglicemic agents, ophtalmics, and cardiovasculars.

6. The complex according to claim 1 wherein basic drug is selected from the group consisting of: diltiazem, promethazine, salbutamol, chlorpheniramine and pharmaceutically acceptable salts thereof.

7. The complex according to claim 1, wherein the carrageenan has a viscosity ranging from 700 to 1600 cPs., measured at 37° C. with a shear rate of 20 s exp(−1).

8. The complex according to claim 7 wherein the carrageenan has a viscosity of 1598 cPs measured at 37° C. with a shear rate of 20 s exp(−1).

9. The complex according to claim 1 wherein the carrageenan is lambda carrageenan.

10. A process for preparing the complex according to claim 1, comprising the following steps:

a. preparing a homogeneous mixture of drug and carrageenan in suitable quantities in order to obtain a final carrageenan complex wherein the drug is contained amounts comprised between 1.5 and 5 mmol/g carrageenan;

b. kneading the mixture in a suitable apparatus by adding a water content expressed as weight ratio water/polymer+water soluble basic substance comprised between 1:3 and 3:1, c. optionally washing and product coming from step (b);

d. drying the mixture, and e. milling the dried product until reaching the desired particle size.

11. A process for preparing the complex according to claim 1, comprising the following steps:

a) preparing a homogeneous mixture of drug and carrageenan in suitable quantities in order to obtain a final carrageenan complex wherein the drug is contained amounts comprised between 1.5 and 5 mmol/g carrageenan;

b) kneading the mixture in an suitable apparatus by adding a water content expressed as weight ratio water/polymer+water soluble basic substance comprised between 1:3 and 3:1, c) optionally washing the product coming from step (b);

d) drying the mixture, and e) milling the dried product until reaching the desired particle size.

12. A controlled release pharmaceutical composition comprising the complex according to claim 1, in combination with suitable excipients and/or diluents.

13. A controlled release pharmaceutical composition comprising the complex according to claim 1.

14. The controlled release pharmaceutical composition according to claim 12 wherein the complex is contained in amounts ranging from 80 to 100% by weight based on the total composition weight.

15. The controlled release pharmaceutical composition according to claim 12, optionally containing up to 5% by weight based on the total composition weight of a gellable polymer selected from the group consisting of hydroxypropylmethylcellulose, and hydroxypropylcellulose having a viscosity between 4000 and 100,000 cPs.

16. The controlled release pharmaceutical composition according to claim 12, optionally containing up to 5% by weight based on the total composition weight of a gellable polymer selected from the group consisting of hydroxypropylmethylcellulose, hydroxypropylcellulose having a viscosity comprised between 4000 and 100,000 cPs.

17. The controlled release pharmaceutical composition according to claim 12 in the form of tablets, pellets and granules.

18. The controlled release pharmaceutical composition according to claim 13 in the form of tablets, pellets and granules.

19. process for preparing the controlled release pharmaceutical compositions in the form of tablets according to claim 17, comprising directly compressing a complex of carrageenan having a viscosity comprised between 500 and 2000 cPs measured at 37° C. with a shear rate of 20 s$^{-1}$, with a soluble drug in powder form with an average particle size ranging from 10 to 100μ and the basic water soluble drug is contained in the complex in amounts ranging from 1.5 to 5 mmol/g carrageenan.

20. A process for preparing the controlled release pharmaceutical compositions in the form of tablets according to claim 18 comprising directly compressing and complex.

21. The controlled release pharmaceutical compositions according to claim 17 in the form of granules having an average particle size ranging from 0.2 to 1 mm.

22. A process for preparing the controlled release pharmaceutical compositions in the form of granules or in the form of pellets according to claim 17 comprising the following steps:

(i) kneading the carrageenan complex powder according to the present invention with an alcoholic solvent in the presence of a binder such as ethyl or methylcellulose having a viscosity ranging from 10 to 100 cPs, (ii) granulating the kneaded mixture in a suitable granulator, (iii) drying the wet granules or pellets, and (iv) classification of the granules or the pellets to separate the granules or pellets having the desired average particle size.

23. A process for the preparation of the tablets according to claim 17 comprising i') preparing the granules by:

(i) kneading the carrageenan complex powder according to the present invention with an alcoholic solvent in the presence of a binder such as ethyl or methylcellulose having a viscosity ranging from 10 to 100 cPs, (ii) granulating the kneaded mixture in a suitable granulator, (iii) drying the wet granules or pellets, (iv) classification of the granules or the pellets to separate the granules or pellets having the desired average particle size; and ii') compressing the granules coming from step (i') to form tablets.

24. A controlled release pharmaceutical composition in the form of a tablet containing:

a. a core, and b. an external layer completely or partially covering the core tablet containing the carrageenan complex with the basic water soluble drug according to claim 1, said external layer being applied by compression.

25. The controlled release pharmaceutical composition according to claim 24 wherein the external layer contains the complex in amounts ranging from 60 to 100%.

26. The controlled release pharmaceutical composition according to of claim 24 containing the complex, in amounts ranging from 80 to 100%.

27. The controlled release pharmaceutical composition according to of claim 24 optionally containing up to 5%, by weight based on the total composition weight of a gellable polymer selected from the group consisting of hydroxypropylmethylcellulose and hydroxypropylcellulose having a viscosity comprised between 4000 and 100,000 cPs, in order to further modulate the drug release.

28. The controlled release pharmaceutical composition according to claim 25 optionally containing up to 5%, by weight based on the total composition weight of a gellable polymer selected from the group consisting of hydroxypropylmethylcellulose, hydroxypropylcellulose having a viscosity comprised between 4000 and 100,000 cPs., in order to further modulate the drug release.

* * * * *

UNITED STATES PATENT AND TRADEMARK OFFICE
CERTIFICATE OF CORRECTION

PATENT NO.   : 6,355,272 B1
DATED        : March 12, 2002
INVENTOR(S)  : Carla Marcella Caramella et al.

It is certified that error appears in the above-identified patent and that said Letters Patent is hereby corrected as shown below:

Title page,
Item [54], the word "PHARAMACEUTICAL" should be -- PHARMACEUTICAL --.

Column 9,
Line 49, insert -- A -- at beginning of claim.

Column 10,
Line 49, delete the word "of" following "according to".

Signed and Sealed this

Twenty-seventh Day of August, 2002

Attest:

Attesting Officer

JAMES E. ROGAN
*Director of the United States Patent and Trademark Office*